US008709190B2

(12) United States Patent
Hunkeler et al.

(10) Patent No.: US 8,709,190 B2
(45) Date of Patent: Apr. 29, 2014

(54) METHOD AND APPARATUS FOR PRODUCING STACKS WHICH FORM BOOK BLOCKS

(75) Inventors: Franz Hunkeler, Wikon (CH); Kurt Graber, Wikon (CH)

(73) Assignee: Hunkeler AG, Wikon (CH)

( * ) Notice: Subject to any disclaimer, the term of this patent is extended or adjusted under 35 U.S.C. 154(b) by 423 days.

(21) Appl. No.: 12/461,541

(22) Filed: Aug. 14, 2009

(65) Prior Publication Data

US 2010/0051196 A1 Mar. 4, 2010

(30) Foreign Application Priority Data

Aug. 29, 2008 (EP) .................................... 08015255

(51) Int. Cl.

| | |
|---|---|
| ***A61F 13/15*** | (2006.01) |
| ***B29C 65/00*** | (2006.01) |
| ***B32B 37/00*** | (2006.01) |
| ***B32B 38/04*** | (2006.01) |
| ***B32B 38/14*** | (2006.01) |
| ***B32B 7/14*** | (2006.01) |
| ***B41F 13/54*** | (2006.01) |
| ***B65H 33/04*** | (2006.01) |
| ***B65H 39/00*** | (2006.01) |
| ***B42C 9/00*** | (2006.01) |

(52) U.S. Cl.

USPC ........... 156/227; 156/267; 156/277; 156/291; 270/1.01; 270/58.08; 412/8

(58) Field of Classification Search

USPC ......... 156/60, 91, 92, 93, 196, 227, 250, 256, 156/264, 277, 288, 290, 291, 295, 349, 350, 156/353, 356, 357, 362, 363, 364, 384, 387, 156/443, 510, 512, 516, 517, 538, 539, 556, 156/558, 559, 563, 566, 578, 267; 270/1.01, 52.01, 52.14, 52.18, 58.01, 270/58.07, 58.08; 412/1, 8, 9, 33, 37

See application file for complete search history.

(56) References Cited

U.S. PATENT DOCUMENTS

| | | | | |
|---|---|---|---|---|
| 4,540,458 | A * | 9/1985 | Baughman et al. | ........... 156/312 |
| 2001/0048862 | A1 * | 12/2001 | Baumann et al. | ................. 412/4 |
| 2003/0062132 | A1 * | 4/2003 | Silverbrook | .................. 156/384 |
| 2005/0161150 | A1 * | 7/2005 | Kruchko | ........................ 156/182 |
| 2007/0031211 | A1 * | 2/2007 | Schmidkonz | ...................... 412/6 |
| 2007/0179037 | A1 | 8/2007 | Dobrovolsky | |

FOREIGN PATENT DOCUMENTS

| | | | |
|---|---|---|---|
| EP | 0 791 478 | A1 | 8/1997 |
| EP | 1 593 621 | A1 | 11/2005 |
| EP | 1 955 865 | A1 | 8/2008 |
| WO | WO 02/40282 | A1 | 5/2002 |
| WO | WO 2004/041545 | A1 | 5/2004 |
| WO | WO 2005/072980 | A2 | 8/2005 |

* cited by examiner

*Primary Examiner* — Philip Tucker
*Assistant Examiner* — Brian R Slawski
(74) *Attorney, Agent, or Firm* — Oliff PLC

(57) ABSTRACT

In order to form stacks, of which each forms a book block, folded sheets are provided with an adhesive application or layer of adhesive before they are placed on one another. Said adhesive application is applied to the sheets adjacent to the folded edge of said sheets and extends in the direction of said folded edge which comes to lie in the spine of the book block. The adhesive can be applied as a continuous track or as a track which is interrupted multiple times, or else in a punctiform manner. The sheets are joined to one another in the stack by means of said adhesive application, with the result that they maintain their position within the stack during further transport of the stack.

10 Claims, 4 Drawing Sheets

Figures 1, 2, 3:
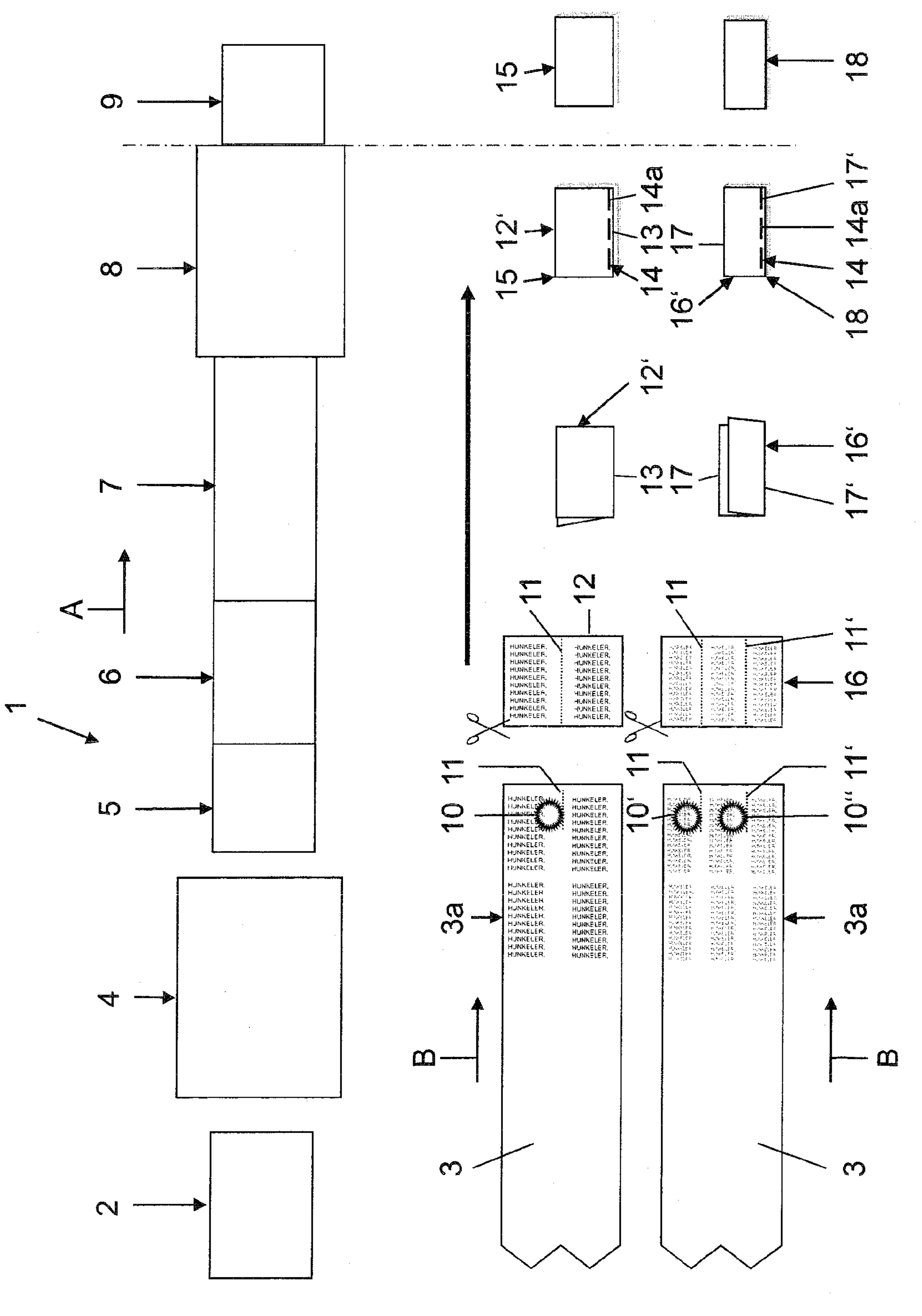

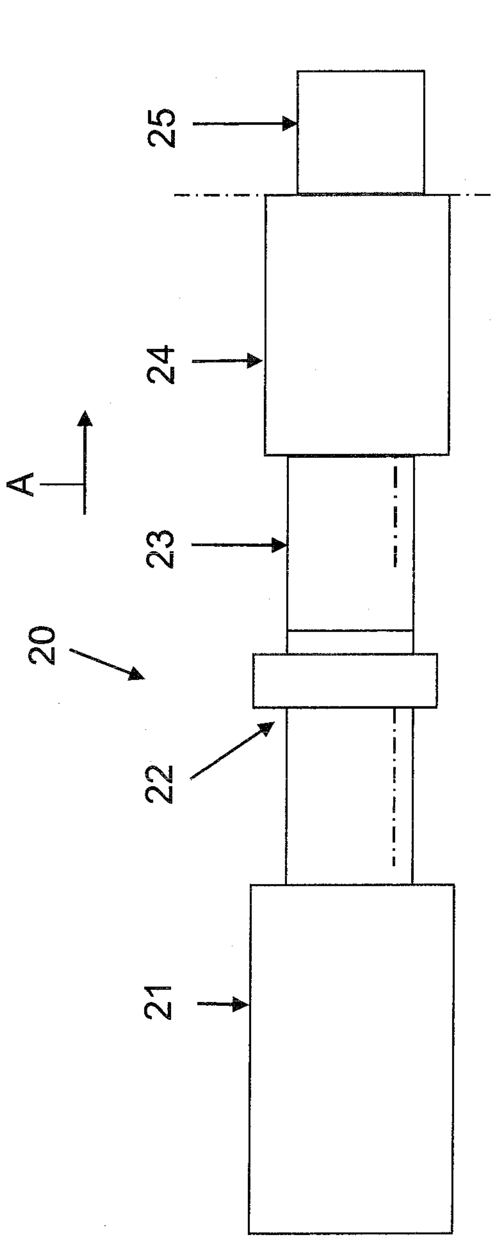
Fig. 4
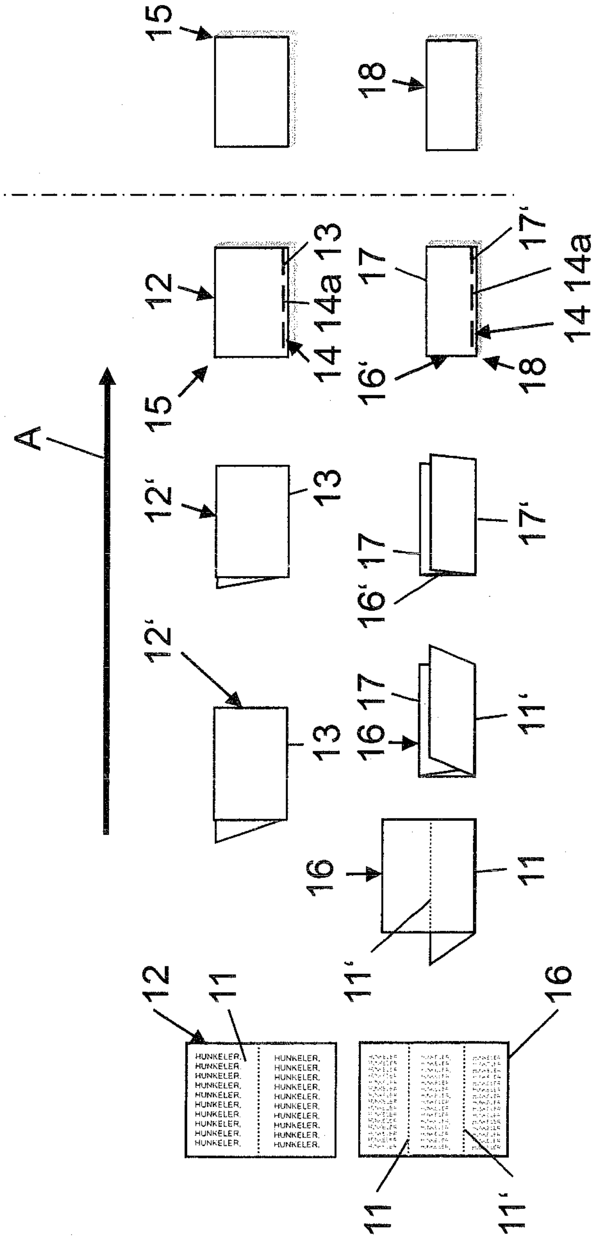
Fig. 5
Fig. 6

METHOD AND APPARATUS FOR PRODUCING STACKS WHICH FORM BOOK BLOCKS

The present invention relates to a method and to an apparatus for producing stacks which form book blocks according to the preamble of claim 1 and the preamble of claim 11, respectively.

US-A-2007/0179037 the disclosure of which is incorporated by reference describes a processing line, in which a material web which is unwound from a reel is printed in a digital printing station. Printed sheets are subsequently separated from the material web by cross cutting, which sheets are folded once or twice. The folded sheets are then placed on one another in a stacking station to form stacks, of which each forms a book block. The stacks are conveyed from the stacking station either to a binding machine or to an intermediate store, from where the stacks are later transported to a binding machine.

During the transport of the stacks from the stacking station to the binding machine or to the intermediate store, it can readily occur that individual sheets are displaced within the stack and thus the precise alignment of the sheets which is present after the stacking is lost in the stack. The binding machines are therefore as a rule equipped with a vibratory apparatus, in which the sheets within one stack are aligned again as accurately as possible in the delivered stacks, in order that very satisfactory binding quality can be achieved.

The present invention is then based on the object of providing a method and an apparatus of the type mentioned in the introduction, which method and apparatus make it possible to retain the precise alignment of the sheets within the stacks which is achieved when the printed sheets are placed on one another, during further transport of the stacks.

According to the invention, this object is achieved by way of a method having the features of claim 1 and by way of an apparatus having the features of claim 11.

The fact that the individual sheets within a stack which forms a book block are joined to one another by means of an adhesive which is applied to the sheets adjacent to a side edge of the sheets, preferably that side edge which comes to lie in the spine of the book block, before or while the sheets are placed on one another achieves a situation where the sheets retain their position within the stack even after leaving the stacking station. This means that the stack quality of the stacks which are fed to the binding machine does not differ from the stack quality of the stacks which are formed in the stacking station.

Since the adhesive application or layer of adhesive is preferably situated on the sheets adjacent to that side edge of the sheets which comes to lie in the spine of the book block, said adhesive application does not have a disadvantageous effect on the quality of the finished book.

Preferred further developments of the method according to the invention and of the apparatus according to the invention form the subject matter of the dependent claims.

Figure 9:
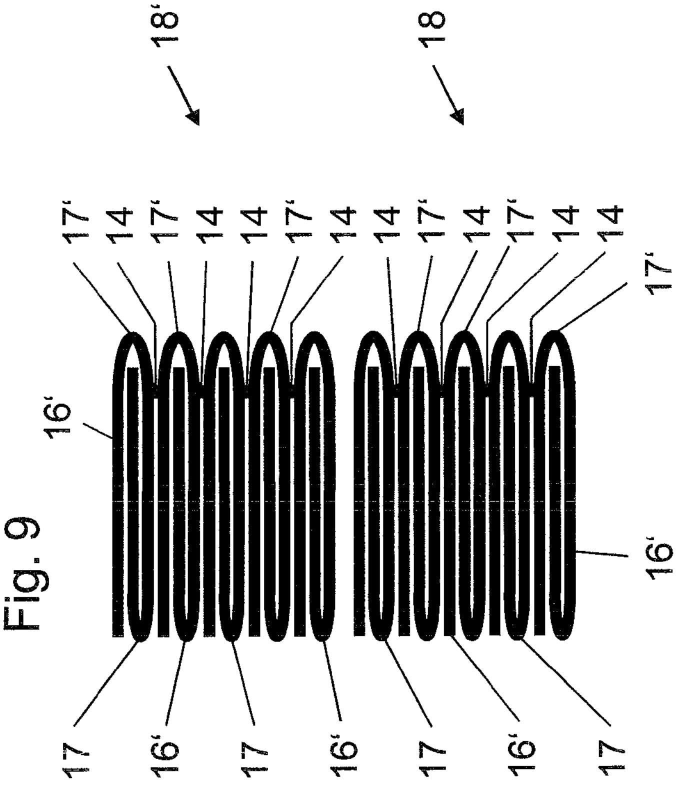
Figure 10:
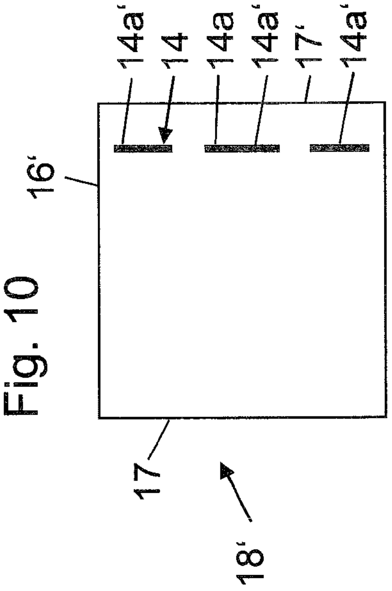
Figure 7:
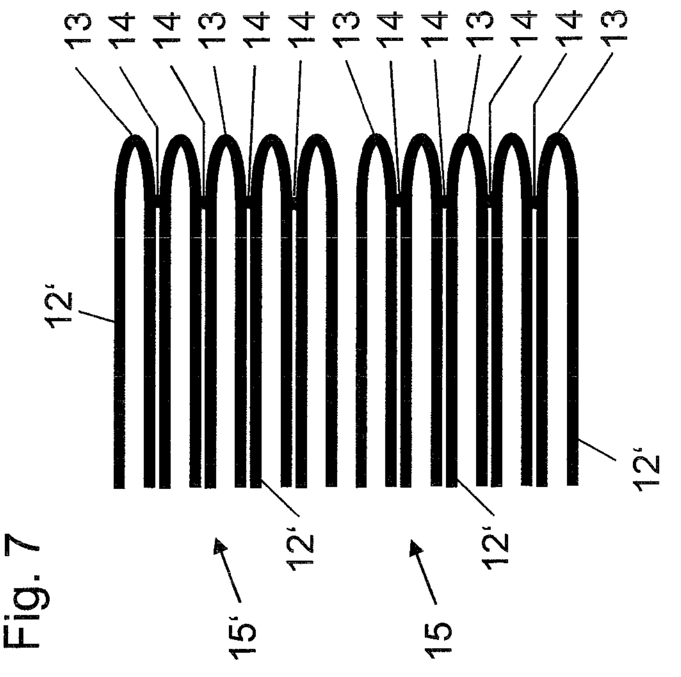
Figure 8:
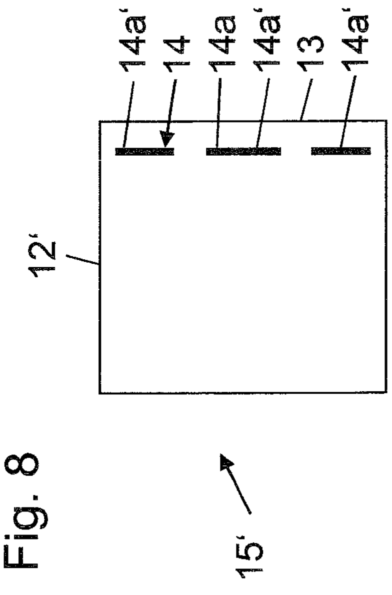
Figure 12:
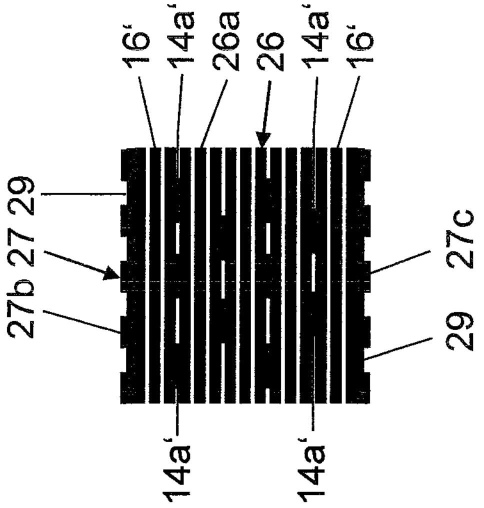
Figure 11:
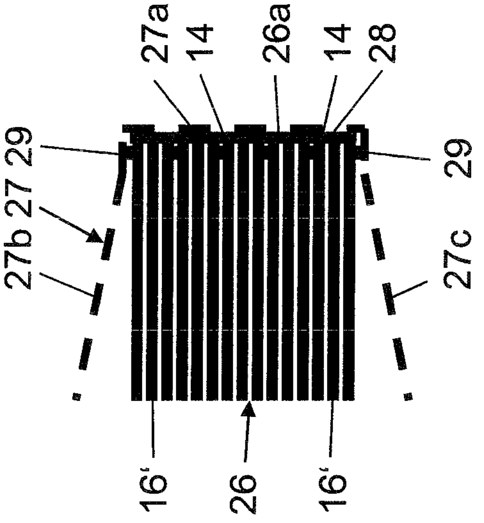

In the following text, the invention will be explained in greater detail using the drawings, in which, purely diagrammatically:

FIG. 1 shows, in plan view, a first embodiment of an apparatus for forming stacks which form book blocks, FIG. 2 shows, in plan view, the production of stacks by means of the apparatus according to FIG. 1 from sheets which are folded once, FIG. 3 shows, in plan view, the production of stacks by means of the apparatus according to FIG. 1 from sheets which are folded twice, FIG. 4 shows, in plan view, a second embodiment of an apparatus for forming stacks which form book blocks, FIG. 5 shows, in plan view, the production of stacks by means of the apparatus according to FIG. 4 from sheets which are folded once, FIG. 6 shows, in plan view, the production of stacks by means of the apparatus according to FIG. 4 from sheets which are folded twice, FIG. 7 shows, in a side view, a stack comprising sheets which are folded once and are joined to one another by means of an adhesive, FIG. 8 shows the stack according to FIG. 7 in plan view, FIG. 9 shows, in a side view, a stack comprising sheets which are folded twice and are joined to one another by means of an adhesive, FIG. 10 shows the stack according to FIG. 9 in a plan view, FIG. 11 shows, in a side view, a finished book block having a cover, and FIG. 12 shows a view of the spine of the book block according to FIG. 11.

The first embodiment (shown diagrammatically in FIG. 1) of an apparatus 1 for producing stacks which form book blocks has, as viewed in the processing direction A, an unwinding station 2, in which the material web 3 (FIGS. 2 and 3) to be processed is unwound from a reel, and a digital printing station 4, in which the material web 3 is printed on both sides. In FIGS. 2 and 3, the printed region of the material web 3 is denoted by 3*a*. A perforating station 5 is connected behind the digital printing station 4, which perforating station 5 has a perforating unit, by means of which the printed material web 3 can be provided with one or two perforation or weakening lines, as will be explained in greater detail using FIGS. 2 and 3. For example, the perforating unit which is marketed by the company Hunkeler AG under the name "Perforating module LP4" can be used as perforating station 5. However, this perforating station 5 can also be omitted.

As viewed in the processing direction A, the perforating station 5 is followed by a cross cutting station 6, in which individual printed sheets are separated from the material web 3 by cross cutting. The cross cutting station 6 is followed by a longitudinal folding station 7, in which the sheets are either folded once or twice, as will be described in even greater detail using FIGS. 2 and 3. The longitudinal folding station 7 is preferably changed over from single folding to double folding and vice versa dynamically during operation, without it being necessary for the longitudinal folding station 7 to be stopped. The longitudinal folding module which is marketed by the company Hunkeler AG under the name "Flyfolder FB6" is particularly suitable as longitudinal folding station 7.

As viewed in the processing direction A, a stacking station 8 is arranged behind the longitudinal folding station 7, in which stacking station 8 the folded sheets are placed on one another to form a stack. Said stacking station 8 has an adhesive application device, by means of which the sheets are provided with an adhesive application or a layer of adhesive before the sheets are placed on one another in a manner which is still to be described. The stacking apparatus which is described in EP-A-1 593 621, supplemented by an adhesive application device, can be used as stacking station 8. 9 denotes a delivery station which accepts the stacks which are formed in the stacking station 8 and guides them away for further processing.

Using FIG. 2, the production of stacks from sheets which are folded once by means of the apparatus 1 which is shown in FIG. 1 will now be described.

The material web 3 which is advanced in the direction of the arrow B, leaves the digital printing station 4 and is printed on both sides is provided with a perforation or weakening line 11 in the perforating station 5 by means of a perforating tool 10 (shown only diagrammatically) which belongs to the perforating unit, which perforating or weakening line 11 extends parallel to the advancing direction B and in the longitudinal direction of the material web 3.

In the following cross cutting station 6, the material web 3 is cut transversely with respect to the advancing direction B and individual sheets 12 are separated from the material web 3. Said sheets 12 are folded once along the perforation line 11 in the longitudinal folding station 7. The sheet which is folded once is denoted by 12' and its folded edge is denoted by 13. Here, these sheets 12' which have been folded once are produced substantially in the same way as described in connection with FIGS. 1 and 2a of US-A-2007/0179037.

In the stacking station 8, the incoming folded sheets 12' are provided with an adhesive application 14 adjacent to its folded edge 13, which adhesive application 14 extends along the folded edge 13 and is an adhesive track 14*a* which is interrupted multiple times in the exemplary embodiment shown. The adhesive is applied before or while the sheets 12' are placed on one another to form a stack.

The sheets 12' which are provided with the adhesive application 14 are then placed on one another in the stacking station 8 to form a stack 15 which is shown in plan view in FIG. 2. The finished stacks 15, in which the sheets 12' which lie above one another are joined to one another, as described, are accepted by the delivery station 9 and guided either into an intermediate store or to a binding station, as is described in US-A-2007/0179037 which has already been referred to earlier.

FIGS. 7 and 8 show, in a side view and in a plan view, two stacks 15, 15' which are arranged above one another to form a large stack and of which each forms a book block and comprises sheets 12' which are folded once. The sheets 12' within one stack 15, 15' are joined to one another by means of the adhesive application 14. Thanks to this connection, the sheets 12' retain their position in the stack 15, 15' during transporting of the stack 15, 15'. As a result, the stack quality which is achieved in the stacking station 8 is maintained during further processing.

As has already been mentioned, the adhesive application 14 is situated adjacent to the folded edge 13. The folded edges 13 come to rest in the spine of the book blocks which are formed by in each case one stack 15, 15', and therefore in the spine of the finished book. The adhesive application 14 therefore does not have a disadvantageous effect on the quality of the finished book. As a rule, the adhesive applications 14 are even removed during the processing of the book block spine.

It can be seen from FIG. 7 that the uppermost sheet 12' in the stack 15, 15' does not have a glue application. It can be seen from FIG. 8 that the glue application 14 is applied as an adhesive track 14*a* which is interrupted multiple times and comprises a plurality of adhesive stripes 14*a'* which are spaced apart from one another.

Using FIG. 3, it will now be described how stacks are produced by means of the apparatus according to FIG. 1 from sheets which are folded twice. Here, reference is made to the preceding description of FIG. 2.

The material web 3 which is printed on both sides in the digital printing station 4 is provided in the perforating station 5 with two perforation or weakening lines 11, 11' which extend parallel to one another and at a spacing from one another in the longitudinal direction of the material web 3, that is to say parallel to the advancing direction B of the material web 3. In order to produce these perforation lines 11, 11', the perforating unit of the perforating station 5 has two perforating tools 10', 10". The switchover from one active perforating tool 10 to two active perforating tools 10', 10" takes place dynamically during operation, that is to say without the perforating station 5 being switched off.

In the same way as described using FIG. 2, individual sheets 16 which are provided with two perforation lines 11, 11' are separated from the material web 3 in the cross cutting station 6. In the longitudinal folding station 7, the sheets 16 are then folded twice about one perforation line 11 and the other perforation line 11' (winding fold). The sheets which are folded twice are denoted by 16' and their folded edges are denoted by 17, 17'. The described production of sheets 16' which are folded twice corresponds to the method of production which is described in connection with FIGS. 1 and 2c of US-A-2007/0179037.

In the same way as described using FIG. 2, the folded sheets 16' are provided with an adhesive application 14 in the stacking station 8 before or while they are placed on one another, which adhesive application 14 extends adjacent to one folded edge 17' and along the latter. Here too, the adhesive application 14 is an adhesive track 14*a* which is interrupted multiple times.

The sheets 16' which are provided with an adhesive application 14 are then placed on one another to form stacks 18 which are guided away via the delivery station 9.

FIGS. 9 and 10 show, in a side view and in plan view, two stacks 18, 18' which are arranged above one another to form a large stack and of which each forms a book block and comprises sheets 16' which are folded twice. In the same way as in the stacks 15, 15' which are shown in FIGS. 7 and 8, the sheets 16' within one stack 18, 18' are joined to one another by means of an adhesive application 14. As already mentioned, this adhesive application 14 lies adjacent to the folded edge 17'. The folded edges 17' come to lie in the spine of the book blocks which are formed by in each case one of the stacks 18, 18'. This results in the same advantages as in the stacks 15, 15' and described in connection with FIGS. 7 and 8.

Now, a second exemplary embodiment of the subject matter of the invention will be described on the basis of FIGS. 4-6. Said second exemplary embodiment differs from the first exemplary embodiment according to FIGS. 1-3 substantially in that individual sheets and not a continuously moved material web 3 are printed in the digital printing station.

The apparatus 20 which is shown in plan view in FIG. 4 for producing stacks which form book blocks, starting from printed individual sheets, has a digital printing station 21 for printing individual sheets. As viewed in the processing direction A, the digital printing station 21 is followed by a longitudinal folding station 22. Said longitudinal folding station 22 is a convertible pocket folder, in which the printed sheets are folded once or twice. An aligning station 23 for the folded sheets is connected behind the longitudinal folding station 22. The aligning station 23 is adjoined by a stacking station 24 having a glue application device, which stacking station 24 corresponds to the stacking station 8 of the apparatus 1 according to FIG. 1. A delivery station 25 which corresponds to the delivery station 9 of the apparatus 1 according to FIG. 1 is arranged behind said stacking station 24.

The production of stacks by means of the apparatus 20 according to FIG. 4 from sheets which are folded once will now be explained using FIG. 5. The production method which is shown in FIG. 5 corresponds largely to the production method which is described using FIG. 2. Reference is therefore also made to said FIG. 2.

As already mentioned, individual sheets 12 are printed on both sides in the digital printing station 21. The printed sheets 12 are provided with a perforation or weakening line 11 which extends parallel to the processing direction A in a perforating station (not shown in FIG. 4) which is arranged between the digital printing station 21 and the pocket folder 22 and corresponds to the perforating station 5 of the apparatus 1 according to FIG. 1. The sheets 12 are folded once along the perforation line 11 in the pocket folder 22. As in FIG. 2, the sheet which is folded once is denoted by 12' and its folded edge is denoted by 13.

The folded sheets 12' are then provided adjacent to the folded edge 13 with an adhesive application 14 in the form of an adhesive track 13*a* which is interrupted multiple times, in the same way as described using FIG. 2. The sheets 12' are then placed on one another to form stacks 15. The finished stacks 15, 15' correspond to the stacks 15, 15' which are shown in FIGS. 7 and 8. Reference is therefore made to the preceding description of said FIGS. 7 and 8.

FIG. 6 shows how stacks are produced by way of the apparatus 20 according to FIG. 4 from printed sheets which are folded twice. Here, this production method corresponds largely to the production method which is described using FIG. 3. For this reason, reference is also made to said FIG. 3.

The sheets 16 which are printed on both sides in the digital printing station 21 are provided with two perforation or weakening lines 11, 11' which extend parallel to one another and at a spacing from one another, in the perforating station (not shown in FIG. 4) which has already been mentioned in conjunction with FIG. 5. In the convertible pocket folder 22, the sheets 16 are folded about one perforation line 11 and then about the other perforation line 11' (letter fold or parallel fold). The pocket folder 22 is preferably changed over from single folding to double folding dynamically during operation, that is to say without the pocket folder being switched off. In the same way as in FIG. 3, the sheet which is folded twice is denoted by 16' and its folded edges are denoted by 17 and 17'.

In the same way as described using FIG. 3, the folded sheets 16' are provided with an adhesive application 14 which extends adjacent to the folded edge 17' and is an adhesive track 14*a* which is interrupted multiple times. The sheets 16' are then placed on one another to form stacks 18. The finished stacks 18, 18' correspond to the stacks 18, 18' which are shown in FIGS. 9 and 10. For this reason, reference is made to the preceding description of said FIGS. 9 and 10.

FIGS. 11 and 12 show, in a side view and in a rear view, a finished book block 26 with a cover 27. The cover 27 is shown using a dashed line and its spine is omitted in the illustration of FIG. 12, in order to make the spine 26*a* of the book block 26 visible.

The book block 26 which is shown is formed by the stack 18 shown in FIG. 9 and comprises sheets 16' which lie on one another and are joined to one another by means of the adhesive application 14. The book block 26 has been processed on its side faces. Here, the folded edges 17 and if applicable also the folded edges 17' have been removed. The book block 26 is fitted into a cover 27 and is joined to the spine 27*a* and the covers 27*b*, 27*c* by means of adhesive connections 28 and 29.

FIG. 12 shows a particularly advantageous distribution of the adhesive stripes 14*a*' (see also FIGS. 8 and 10). The adhesive stripes 14*a* on a sheet are namely offset laterally with respect to one another in the transverse direction with respect to the book block spine 26 and therefore in the direction of the side edges of the sheets 16', with respect to the adhesive stripes 14*a*' of the sheet which lies underneath. This distribution of the adhesive stripe 14*a*' in the stack 18, 18' and in the book block 26 achieves a situation where not all the adhesive stripes 14*a*' lie directly above one another. The effects of the adhesive stripes 14*a*' on the height of the stack 18 can therefore be kept low. The same is naturally also true for the stacks 15, 15' which are shown in FIG. 7.

In the exemplary embodiments which are described in the preceding text, the adhesive application 14 comprises an adhesive track 14*b* which is formed by individual adhesive stripes 14*a*' which are arranged at a spacing from one another. However, it is also possible to apply the adhesive as an uninterrupted, continuous track. However, the adhesive can also be applied in a punctiform manner.

A dispersion adhesive is very particularly suitable as adhesive. An adhesive of this type joins the sheets sufficiently quickly and without artificial drying.

The adhesive is applied by means of suitable adhesive application devices which are known per se. In order to apply the adhesive, the sheets are moved along by adhesive application elements, for example nozzles. Adhesive is dispensed from the adhesive application elements as dots, individual stripes or a continuous stripe on account of control commands, as has already been described. The control commands for the adhesive application device can be generated by the digital printing station 4, 21. In addition, a bar code which is printed onto the sheets can also be used to control the adhesive application device.

The adhesive application device can be integrated into the stacking station 8, 24 or can be arranged upstream of the stacking apparatus.

Individual stacks 15, 18 are produced in the stacking station 8, 24 and are then fed to the delivery station 9, 25. However, it is also possible to form a plurality of stacks 15, 15' and 18, 18' which lie on one another in the stacking station 8, 24 (see FIGS. 7 and 9) and to feed the large stack which is formed by the stacks 15, 15'; 18, 18' which lie on one another to the delivery station 9, 25. Individual stacks are as a rule transported directly to a binding machine, while large stacks are moved into an intermediate store.

The production methods which are described using FIGS. 2 and 3 and/or 5 and 6 can also be carried out by way of other apparatuses than the apparatuses 1, 20 which are shown in FIGS. 1 and 4. Thus, in the apparatus 1 according to FIG. 1, a plough fold device can be used as longitudinal folding device 7 instead of, as mentioned, a "Flyfolder FB6" from the company Hunkeler AG.

The production method according to the invention has been explained in the preceding text starting from folded sheets 12', 16'. However, it is also possible to stack unfolded individual sheets in the described way and to provide them with an adhesive application before they are placed on one another. In the case of books above a certain page number, however, this could lead to difficulties because the adhesive applications on each individual sheet take up to much space over the height of the stack, which has a disadvantageous effect on the stack quality. This disadvantage is of consequence, above all, in the case of thin individual sheets.

In the apparatus which is shown in FIG. 4 and in the corresponding method which is shown in FIGS. 5 and 6, the perforating station and/or the perforating can be dispensed with if sheets which are already perforated are fed to the digital printing station 21.

In the apparatus which is shown in FIG. 1 and in the corresponding method which is shown in FIGS. 2 and 3, it would also be conceivable to feed a material web 3 which has already been perforated in the longitudinal direction to the digital printing station 4. To this end, the perforating station 5 could be arranged upstream of the digital printing station 4, or a perforating station 5 of this type could be dispensed with if the material web 3 which is wound onto the reel of the unwinding station 2 is already perforated.

In the exemplary embodiments which are shown, the adhesive is applied adjacent to that side edge which comes to lie in the spine of the book block. However, it is also possible to apply the adhesive adjacent to another side edge. The adhesive application is then cut away later, for example by means of a three knife trimmer.

It is also possible in the method which is described, as is generally routine, to cut the finished stacks 15, 18 on that side which comes to lie in the spine of the book block 26 during the further processing in a binding station, in particular an adhesive binding station. Here, the adhesive application 14 is removed, which is not disadvantageous, however, since the stacks are held stably in the binding station. The cut spine of the book block can then be joined to the spine of the cover in a known way by means of adhesive connections.

The invention claimed is:

1. A method for producing book blocks, of which each is formed from a stack of sheets which are printed on both sides in a digital printing station, the method comprising;

laying the sheets which are printed on both sides on one another to form stacks, each stack forming a book block;

folding the individual sheets which belong to the same book block once or multiple times about folded edges into folded sheets of two or more leaves including an uppermost and a lowermost leaf, respectively;

applying an adhesive to only one leaf of the folded sheets adjacent to the folded edge of the folded sheets which comes to lie in the spine of the book block before or while the folded sheets are placed on one another to form a stack, wherein each adhesive application connects the uppermost leaf of a folded sheet with the lowermost leaf of the next higher folded sheet in the stack, and wherein the adhesive is applied to an area of the folded sheets which is cut away in a further processing step after placing the folded sheets on one another.

2. The method as claimed in claim 1, wherein the adhesive is applied to the sheets along a side edge.

3. The method as claimed in claim 2, wherein the adhesive is applied as a continuous track.

4. The method as claimed in claim 3, wherein the adhesive is applied in a continuous line.

5. The method as claimed in claim 2, wherein the adhesive is applied in regions which are spaced apart from one another.

6. The method as claimed in claim 5, wherein the adhesive is applied in a punctiform manner or as a track which is interrupted once or multiple times.

7. The method as claimed in claim 5, wherein the adhesive is applied to the individual sheets of a book block in such a way that the adhesive applications are offset with respect to one another in the direction of the side edge on a sheet, with respect to the adhesive applications on the sheet which lies below.

8. The method as claimed in claim 1, wherein a dispersion adhesive is used as adhesive.

9. The method as claimed in claim 1, wherein the folded edges are parallel to one another.

10. The method as claimed in claim 1, wherein each folded edge has a continuous surface.

* * * * *